US007665673B2

(12) United States Patent
Hagleitner

(10) Patent No.: US 7,665,673 B2
(45) Date of Patent: Feb. 23, 2010

(54) METHOD AND APPARATUS FOR SPRAYING PORTIONS OF AN AIR-IMPROVING SUBSTANCE

(75) Inventor: Hans Georg Hagleitner, Zell am See (AT)

(73) Assignee: Hagleitner Hygiene International GmbH, Zell am See (AT)

( * ) Notice: Subject to any disclaimer, the term of this patent is extended or adjusted under 35 U.S.C. 154(b) by 0 days.

(21) Appl. No.: 10/960,003

(22) Filed: Oct. 8, 2004

(65) Prior Publication Data

US 2005/0082383 A1   Apr. 21, 2005

Related U.S. Application Data

(63) Continuation of application No. PCT/AT03/00041, filed on Feb. 12, 2003.

(30) Foreign Application Priority Data

Apr. 19, 2002   (AT) ................................ A 613/2002

(51) Int. Cl.
B67D 5/08   (2006.01)

(52) U.S. Cl. ................................ 239/73; 239/1; 239/67; 239/69; 239/337; 222/639; 700/283

(58) Field of Classification Search ..................... 239/1, 239/11, 67, 69, 70, 73, 337, 373; 222/52, 222/639–642; 137/624.11, 624.2; 700/283
See application file for complete search history.

(56) References Cited

U.S. PATENT DOCUMENTS

| 5,217,035 | A | * | 6/1993 | Van Marcke | .................... 137/1 |
| 5,377,363 | A | * | 1/1995 | Shieh | ............................ 4/313 |
| 6,254,065 | B1 | | 7/2001 | Ehrensperger et al. | |
| 6,267,297 | B1 | | 7/2001 | Contadini et al. | |
| 6,347,414 | B2 | * | 2/2002 | Contadini et al. | ............... 4/222 |
| 6,739,479 | B2 | * | 5/2004 | Contadini et al. | ............... 222/52 |
| 6,938,280 | B2 | * | 9/2005 | Wawrla et al. | .................. 4/304 |
| 2002/0036358 | A1 | | 3/2002 | Watkins | |

* cited by examiner

*Primary Examiner*—Len Tran
*Assistant Examiner*—Jason J Boeckmann
(74) *Attorney, Agent, or Firm*—Wenderoth, Lind & Ponack, L.L.P.

(57) ABSTRACT

A method of spraying an air-improving substance in a room is provided. In particular, persons moving in the room are detected, and a spraying operation is performed while taking into account the detected movement.

8 Claims, 2 Drawing Sheets

METHOD AND APPARATUS FOR SPRAYING PORTIONS OF AN AIR-IMPROVING SUBSTANCE

This application is a continuation application of International Application No. PCT/AT03/00041, filed Feb. 12, 2003.

BACKGROUND OF THE INVENTION

The invention concerns methods and an apparatus for spraying portions of an air-improving substance in a room, in particular in a washroom.

Countless proposals are already known for improving air, in particular, in washrooms, by spraying a deodorizing and/or fragrant substance. These proposals range from spray cans which are fitted to the door and which are actuated when the door is opened or closed (for example GB 411 055 A) to programmable dispensers (for example U.S. Pat. No. 6,267,297 B) in which spray sequences which take place in accordance with various selectable criteria can be predetermined. Those dispensers have adjusting options for the beginning and the end of the spray sequences, for the duration of the time intervals in respect of the spray procedures, for daytime or night operation and so forth, and are provided with an electrical spray knob actuating means, an electronic (time) control, a voltage supply, an illumination sensor, and a device which monitors exhaustion of the fragrance. The number of users and user frequency are in that case only limitedly taken into consideration. They are also detected when washrooms are used without daylight by individual people as switching on the lighting leads to the presumption of a user.

In public washrooms, particularly when there is a high number of users and a fluctuating user frequency, the known apparatuses are unsatisfactory. The spray operations should take place whenever they are necessary, in which respect spray operations should be avoided when users are present in order not to spray the users. A time control cannot establish the presence of one or more users and a brightness control cannot ascertain the number of users.

SUMMARY OF THE INVENTION

The invention now proposes utilizing the movement of persons present, as a further important criterion for triggering the spraying operations. In a first mode of operation of a fragrance dispenser, it is established that persons are moving in the room (i.e., an interrogation area) and that the next spray operation is triggered off only when no further movement of persons is detected. This design configuration affords a pure motion signalling control, in which case a spray operation takes place only when no more movement can be detected (that is to say, when the user or users has or have left the interrogation area).

In a second mode of operation which is based on an interval control, the procedure involves establishing whether persons are moving in the room (i.e., the interrogation area) and the impending spray operation is suppressed if a movement of persons is detected. In this design configuration, the motion signalling is superimposed on the time control and the spray operation takes place at the intended moment in time only when no movement can be detected (that is to say, no user is present). Preferably in that respect time intervals of between 2.5 and 60 minutes can be set, depending on the respective nature of the room (interrogation area). Particularly when prolonged pauses (for example, of 30 minutes) between the spray operations are involved, it is conceivable that no spray operation takes place throughout the entire operating period, as a person is present precisely at each spray time. Therefore, particularly when long time intervals are involved, it is preferably provided that the suppressed spray operation is subsequently implemented when no further movement of persons is detected. In the example specified above, that would increase the interval to 35 minutes, in which case the subsequent spray operations are selectively effected either in the original spray sequence (that is to say, the next pause is reduced to 25 minutes), or the entire spray sequence is shifted by a delay of 5 minutes.

Particularly in public washrooms, an ongoing, high frequency (i.e., high level of traffic) can have the result that a rest condition which is required for the spray operation to be triggered does not occur.

Therefore, in particular in the first mode of operation with relatively short time intervals, but also in the second mode of operation, it is preferably provided that, in the case of movement of persons in the room (interrogation area), which movement continues over a predetermined period of time, a spray operation is triggered off even when movement of persons in the room (interrogation area) is detected. In this third mode of operation, the period of time is preferably also adjustable and includes for example between 2.5 and 15 minutes. If, in the first mode of operation with pure motion signalling control, no rest condition can be ascertained over a predetermined period of time of, for example, 10 minutes, which indicates a high number of users, the spray operation is effected even with the risk that the users who are present at that time are sprayed. If the intensive use continues over a prolonged period of time, for example the entire morning, then once again a spray sequence takes place at equal time intervals. These time intervals, however, as is also necessary by virtue of the high user frequency, are substantially shorter than in the interval control of the second mode of operation, and this is maintained only as long as that user frequency applies.

An apparatus for spraying portions of an air-improving substance, for example a deodorizing substance, a fragrance, or the like, which permits both modes of operation, is provided with a motion sensor. In order to allow a detected person to leave the room (i.e. interrogation area) so that the person is not sprayed (i.e., the person is beyond the reach of the spray), a delay is provided between the detection of a movement and signal delivery for triggering a spray operation. The preferably adjustable delay time is between 15 and 30 seconds. The delay can be adjusted at the motion sensor, depending on the respective design configuration involved, so that the motion signalling to the control takes place with a delay or is set by the control means itself. In both cases, the presence of a moving person is again detected by the motion sensor and the next delay time begins to run, and so forth. Accordingly, the triggering signal for the spray operation is only delivered after motion detection, and possibly even only after repeated motion detection, and only when the movement is already concluded. If the delay takes place at the motion sensor, the control signal of the motion sensor represents a motion end message.

BRIEF DESCRIPTION OF THE DRAWINGS

The invention will now be described in greater detail with reference to the Figures of the accompanying drawings without being limited thereto. In the drawings.

DETAILED DESCRIPTION OF THE INVENTION

Figure 1:
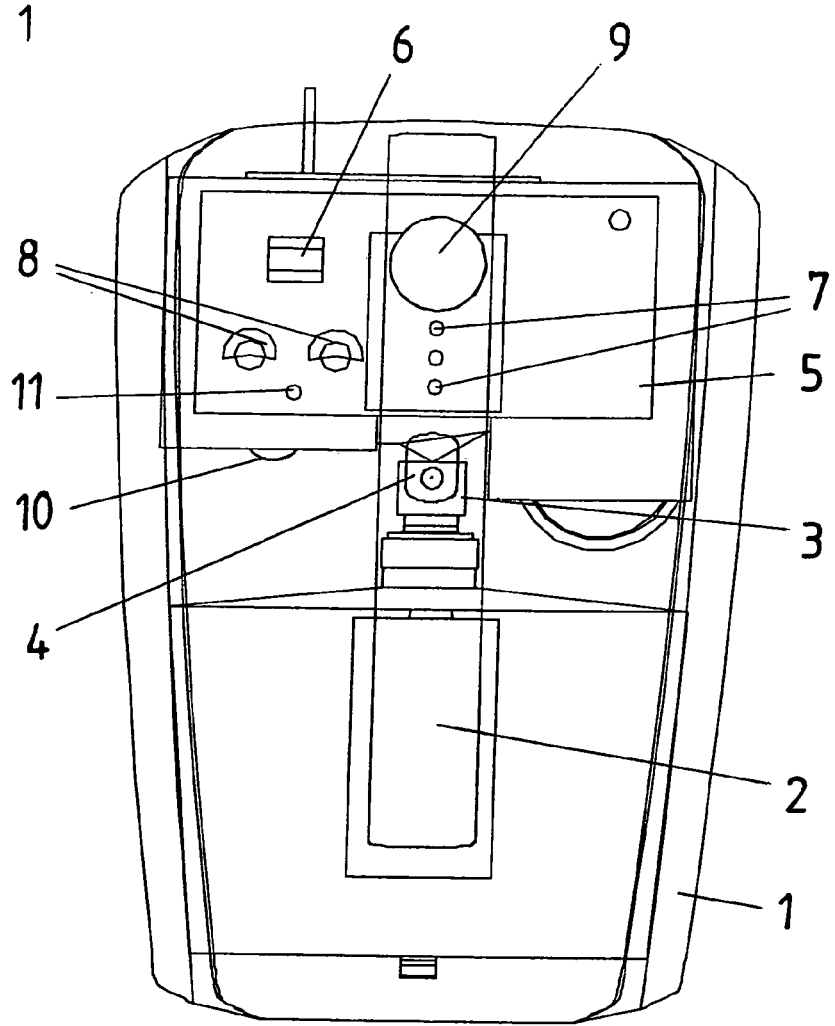
FIG. 1 is a diagrammatic front view of an apparatus according to the invention.

An apparatus for spraying an air-improving substance in a room (i.e., an interrogation area), in particular in a washroom, has a housing 1 which can be fixed to a wall or the like. In the housing 1, there is arranged a replaceable container 2 which is provided with a spray head 3 and which contains an air-improving substance. The content of the container is sprayed out during each spray operation by an auxiliary means through a window 4 of the housing 1, for example by an electrically driven pump device. Batteries or the like (not shown) are contained in the housing 1 as the power source. However, a connection to a power main is also possible.

The housing 1 further includes an electronic controller 5 which includes an operating mode selector switch 6, light emitting diodes 7 for state, filling level and operational display, time setting rotary knobs 8 for setting the intervals in the second and third modes of operation, a motion sensor 9 with a time delay $\Delta t$ for signal delivery (which can be adjusted), and a light-sensitive sensor 11 by way of which it is possible to establish for example day/night operation. Finally, there is also provided a test module switch 10, wherein the basic functions of the apparatus can be tested in a first switch position and the basic settings of the controller 5, the motion sensor 9, the light-sensitive sensor 11 and so forth can be tested in a second switch position.

Figure 2:
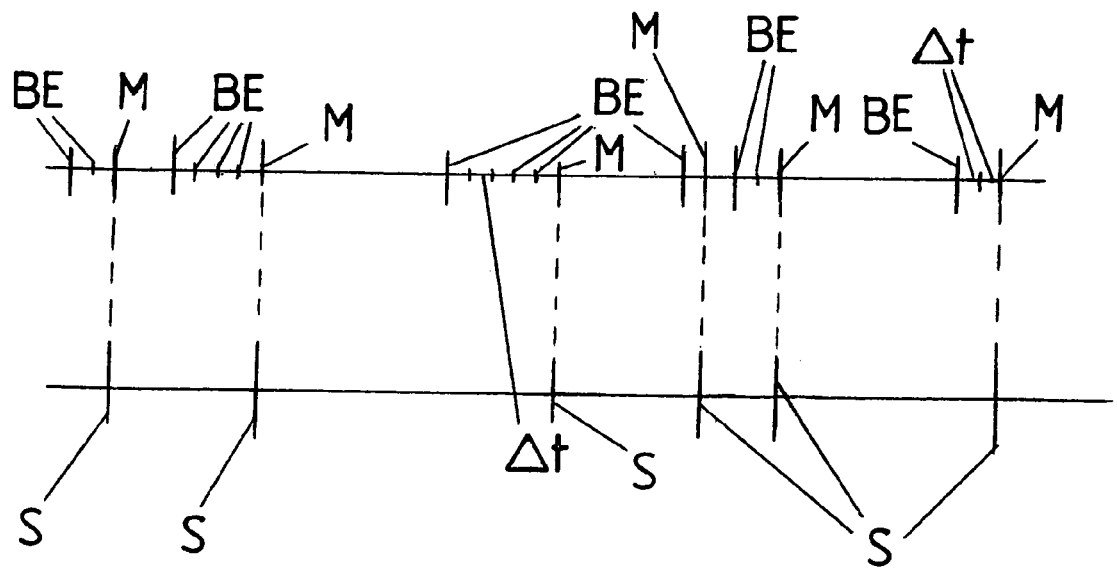
FIGS. 2 through 4 are functional diagrams of three different modes of operation.

The spray apparatus according to the invention for spraying an air-improving substance can be operated in differing ways adapted to the requirements involved by virtue of the motion sensor 9. A functional diagram of the first operating mode is shown in FIG. 2. Each spray operation S is triggered off exclusively as a consequence of a detected movement BE of a user or another person as soon as (after) that movement is no longer detected. For that purpose, a delay time $\Delta t$ can be set at the motion sensor 9. If the motion sensor 9, which is switched to the active condition again subsequent to the delay time $\Delta t$, again detects a movement BE, the next delay time $\Delta t$ begins to run, after which either the notification signal M is transmitted or a movement BE is detected a further time. The delay time $\Delta t$ is selected so that the user can leave the room and he is in no way sprayed with the air-improving substance.

Figure 3:
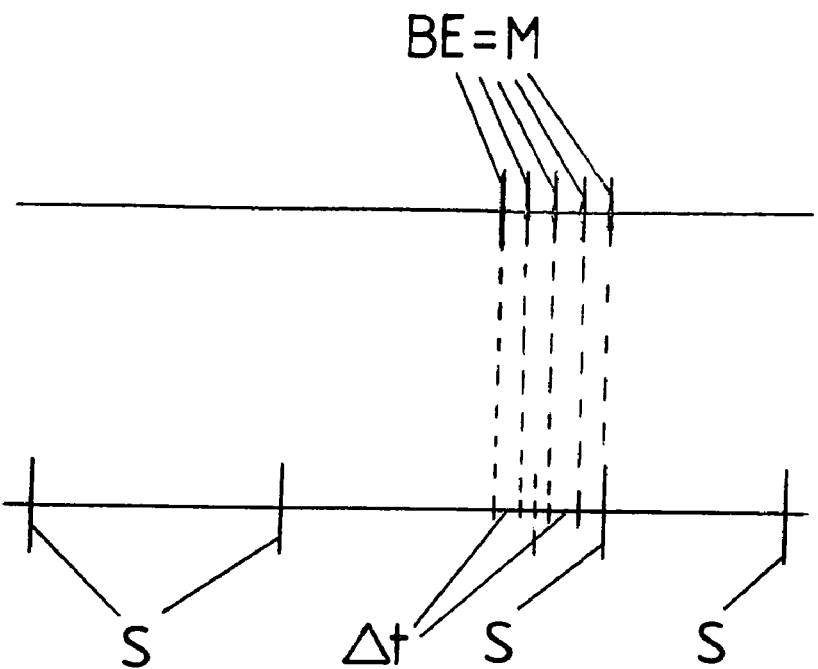

FIG. 3 shows a second mode of operation in which a time interval is predetermined and spray operations S take place automatically at longer intervals if the motion sensor 9 does not deliver a signal. This means that a spray operation is suppressed if a movement BE is detected by the motion sensor 9 just at the intended spray time. Preferably, the suppressed spray operation S is repeated after the end of the movement.

Figure 4:
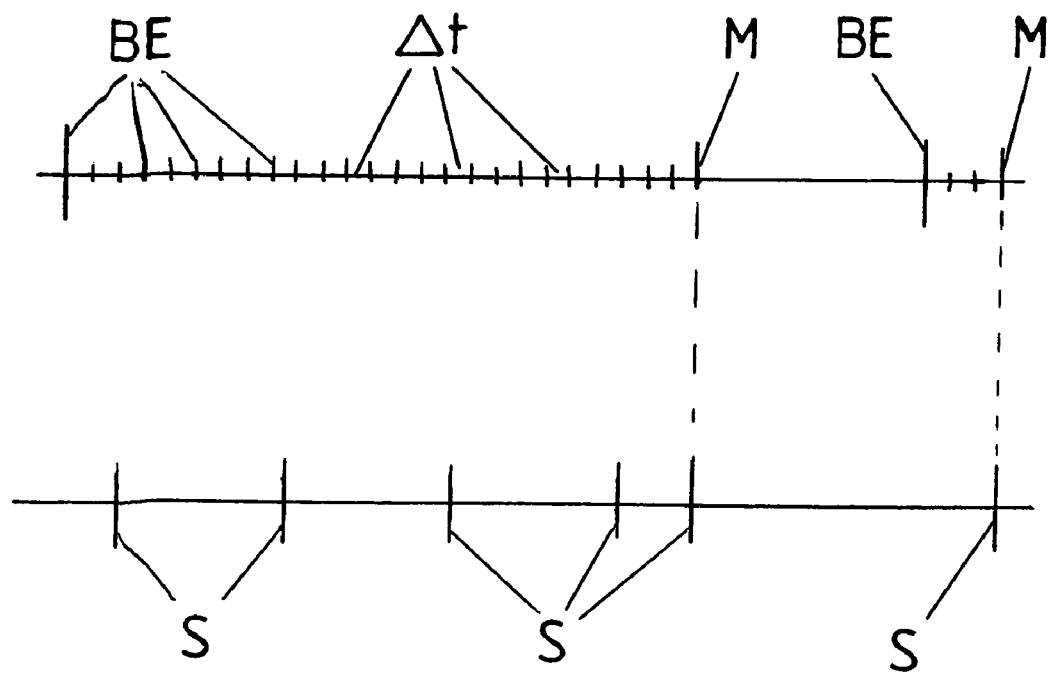

FIG. 4 shows a functional diagram of a third mode of operation which is designed for a very high user frequency (i.e., high traffic). Here, by virtue of a continuously repetitive motion recognition BE over a prolonged period of time there will be no notification signal M for the end of the movement and no spray operation. In that situation, the motion signalling control of FIG. 2 is overridden insofar as a spray operation S takes place after a fixed time (after a maximum amount of delay time) which can be adjusted by means of the rotary knob 8, even though there are people in the room (interrogation area). In other words, after a fixed amount of delay time passes (i.e. the amount of time between a predetermined initial or specific point in time—which is the point in time when the spray operation was initially supposed to occur, as explained above—and an ultimate point in time), the initial override procedure discussed above with respect to FIG. 2 is further overridden such that the spray operation S takes place even if people are still moving in the room.

The invention claimed is:

1. A method of spraying an air-improving substance into an interrogation area, comprising:

defining a predetermined initial point in time when a spray operation is to be performed, the spray operation including spraying the air-improving substance into the interrogation area;

defining an ultimate point in time, the ultimate point in time being a predetermined fixed amount of delay time after the initial point in time;

detecting whether there is movement in the interrogation area at the initial point in time;

performing the spray operation of the air-improving substance into the interrogation area at the initial point in time if no movement is detected in the interrogation area at the initial point in time during said detecting;

delaying the spray operation of the air-improving substance into the interrogation area if movement is detected at the initial point in time during said detecting, said delaying being performed up to the ultimate point in time during periods of continuous movement in the interrogation area;

performing the spray operation if movement is no longer detected in the interrogation area after the spray operation has been delayed at the initial point in time and prior to the ultimate point in time; and performing the spray operation at the ultimate point in time even if movement is still detected in the interrogation area.

2. The method of claim 1, wherein said performing of the spray operation after said delaying of the spray operation if the movement is no longer detected comprises performing the spray operation after a predetermined period of time has elapsed after the movement is no longer detected.

3. The method of claim 1, wherein said detecting comprises using a motion sensor of a spray apparatus to detect movement in the interrogation area, and said delaying comprises using a controller of the spray apparatus to delay an operation of a spray head of the spray apparatus if the movement is detected.

4. The method of claim 1, wherein said detecting comprises detecting whether there is movement of a person in the interrogation area.

5. A method of spraying an air-improving substance into an interrogation area, comprising:

setting a spray sequence for performing a spray operation including defining predetermined specific points in time when the air-improving substance is to be sprayed into the interrogation area, the specific points in time being spaced at equal time intervals;

setting ultimate points in time, each of the ultimate points in time being a predetermined fixed amount of delay time after a respective one of the specific points in time;

detecting whether there is movement in the interrogation area at each of the specific points in time;

performing the spray operation of the air-improving substance into the interrogation area at the specific points in time if no movement is detected in the interrogation area at the specific points in time during said detecting;

suppressing the spray operation of the air-improving substance into the interrogation area at any one of the specific points in time if movement is detected at the any one of the specific points in time during said detecting, said suppressing being performed up to the ultimate point in time for the respective any one of the specific points in time at which movement has been detected during said detecting;

performing the spray operation if movement is no longer detected in the interrogation area after the spray operation has been delayed at the any one of the specific points in time and prior to the ultimate point in time for the respective any one of the specific points in time; and performing the spray operation at the ultimate point in time for the respective any one of the specific points in time even if movement is still detected in the interrogation area.

6. The method of claim 5, wherein said detecting comprises using a motion sensor of a spray apparatus to detect movement in the interrogation area, and said suppressing comprises using a controller of the spray apparatus to suppress an operation of a spray head of the spray apparatus if the movement is detected.

7. The method of claim 5, wherein said detecting comprises detecting whether there is movement of a person in the interrogation area.

8. The method of claim 5, further comprising, if movement has been detected at any one of the specific points in time, performing a spray operation after the any one of the specific points in time and before the ultimate point in time for the respective any one of the specific points in time if the movement is no longer detected.

* * * * *